United States Patent
Gross et al.

(12)
(10) Patent No.: US 6,924,129 B2
(45) Date of Patent: Aug. 2, 2005

(54) ENZYME-CATALYZED ESTERIFICATION OF PENDANT CARBOXYLIC ACID GROUPS

(75) Inventors: Riahcrd A. Gross, Plainview, NY (US); Bishwabhusan Sahoo, Brooklyn, NY (US)

(73) Assignee: Polytechnic University, Brooklyn, NY (US)

( * ) Notice: Subject to any disclaimer, the term of this patent is extended or adjusted under 35 U.S.C. 154(b) by 458 days.

(21) Appl. No.: 10/278,320

(22) Filed: Oct. 23, 2002

(65) Prior Publication Data

US 2004/0082023 A1 Apr. 29, 2004

(51) Int. Cl.$^7$ ............... C12P 19/04; C12P 19/12; C12P 7/62; C12P 13/18; C12F 20/02
(52) U.S. Cl. ............... 435/100; 435/101; 435/110; 435/123; 435/126; 435/128; 435/130; 435/135; 525/330.1; 525/384
(58) Field of Search ............... 435/100, 10, 110, 435/123, 126, 128, 135; 525/330.1, 384

(56) References Cited

U.S. PATENT DOCUMENTS

| | | | |
|---|---|---|---|
| 2,680,735 | A | 6/1954 | Fegley |
| 2,877,215 | A | 3/1959 | Fang |
| 2,967,173 | A | 1/1961 | Fang |
| 2,979,514 | A | 4/1961 | O'Brien |
| 3,530,167 | A | 9/1970 | Dowbenko |
| 4,076,727 | A | 2/1978 | Zey |
| 4,634,722 | A | 1/1987 | Gallop |

*Primary Examiner*—Herbert J. Lilling
(74) *Attorney, Agent, or Firm*—Technoprop Colton LLC

(57) ABSTRACT

A method for enzymatically synthesizing a polymer by combining a preselected quantity of an enzyme, a first reactant selected from polymers with at least one carboxylic acid pendant group, a second reactant selected from alcohols, i.e., polyols, in a reaction vessel; heating the reaction vessel to a preselected temperature; and maintaining the reaction vessel at the preselected temperature for a preselected time with mixing, wherein an esterification reaction results at at least one carboxylic acid pendant group of the polymer with one hydroxyl group from the polyol and results in a modified polymer.

30 Claims, 11 Drawing Sheets

R= $CH_2OH$, -$(CHOH)_nCH_2OH$, $CH(OH)CH_2N(CH_2CH_3)_2$, sugar and its derivatives
n= 1, 2, 3, 4

R'= H, -COOH, Alkyl ($CH_3$-$C_6H_{14}$)

R''= H, COOH, CO
M= -O-, -N-

HMWPAA (Starting Polymer, Polyacrylic acid)    $M_n=(6.22\pm0.08)\times10^4$, $M_w=(1.51\pm0.01)\times10^5$
HMWPAAGLY (Polyacrylic acid modified with glycerol)  $M_n=(1.10\pm0.02)\times10^5$, $M_w=(3.58\pm0.04)\times10^5$

ENZYME-CATALYZED ESTERIFICATION OF PENDANT CARBOXYLIC ACID GROUPS

BACKGROUND OF THE INVENTION

1. Technical Field

The present invention relates to an enzymatic process for preparing and modifying polymers with pendant carboxylic acid groups. More particularly, the present invention relates to a process for modifying the carboxylic acid pendant groups of polymers with hydroxyl groups of alcohols (polyols) through an enzyme-catalyzed esterification with high selectivity.

2. Prior Art

Methods for the preparation and tailoring of polymers through the esterification of pendant groups on the polymers are known in the art. Conventional methods for the direct esterification of acid groups attached as side or pendant groups to polymer chains with a molecule containing an alcohol group suffer from many problems. High reaction temperatures (>200° C.) and the need for acid catalysts for such reactions result in undesirable side reactions such as dehydration of the alcohol, β-scission of ester links to form acid and alkenes, decarboxylation of the acid, and polymerization of alkenes formed. Also, these harsh conditions make it impossible to conduct reactions with groups that are thermally sensitive or are decomposed in the presence of the acid catalyst. For example, the direct esterification of hydrolytically labile main chains bearing carboxylic acid pendant groups would result in deleterious reactions such as extensive hydrolysis of the main chain. An undesirable alternative is the use of stoichiometric quantities of expensive coupling agents such as those containing carbodiimide moieties.

The prior art discloses a number of examples of methods for the introduction of ester bonds onto pendant groups of polymers. However, most of the prior art is related to the preformation of an ester prior to polymerization and not to the enzyme-catalyzed esterification of carboxylic pendant groups of an existing polymer.

U.S. Pat. No. 2,680,735 to Fegley discloses a method for the formation of a monomeric ester bond on a pendant group that requires a tedious protection-deprotection step. The necessity for the use of inhibitors to protect the monomer from premature polymerization and otherwise harsh chemical methods is a relative disadvantage.

U.S. Pat. No. 2,877,215 to Fang discloses a phoshated copolymer in which an ester bond is created on a pendant group through steps also involving a protection-deprotection step and further involving the use of phosphoric acid. U.S. Pat. No. 2,967,173 to Fang and U.S. Pat. No. 2,979,514 to O'Brien disclose the preparation of polymerizable polyhydroxy esters of acrylic acid and methacrylic acid to homopolymers and copolymers with high precaution using phosgene or a lower alkyl ester of chromic acid in the presence of a hydrogen chloride acceptor. U.S. Pat. No. 3,530,167 to Dowbenko also discloses certain acetal-type polymers, and further requires multiple steps for the synthesis using various hazardous chemicals.

U.S. Pat. No. 4,076,727 to Zey discloses preparing cyclic acetals from polyols, but again uses protection-deprotection steps. U.S. Pat. No. 4,634,722 to Gallop discloses copolymers that also are produced using a protecting group, such as an alkyl boronic acid adduct of glyceryl methacrylate or glyceryl acrylate, in combination with an alkyl acrylate or alkyl methacrylate.

Summarily, the prior art methods rely on performing reactions under relatively harsh chemical conditions and/or the use of protection-deprotection methods to prevent side chains from becoming chemically altered. Accordingly, new and more efficient methods for preparing and tailoring polymers with carboxylic acid side groups are constantly being sought.

BRIEF SUMMARY OF THE INVENTION

The present invention relates to a method for modifying the carboxylic acid groups of polymers that proceeds as catalyzed esterification, and to compositions produced from this method. More specifically, the present invention is an efficient and selective method for the modification of polymers with carboxylic acid side chains and new compositions that result from the modification of polymer carboxylic side chains. The catalyzed esterification of the present invention can proceed under bulk flow (solventless) conditions by the direct reaction between the carboxylic acid pendant group of selected polymers and the hydroxyl group of selected alcohols and uses enzyme-catalysis to achieve high selectivity during the modification reaction.

Briefly described, the present invention is an enzymatic process for the preparation and tailoring of polymers with pendant carboxyl acid groups. The process is a one-step enzymatic reaction in which polymers with pendant carboxylic acid groups are combined with alcohols containing at least one hydroxyl group. The present invention makes use of an efficient lipase-catalyzed route for the modification of polymers with pendant carboxylic acid groups. The modifications can be performed with or without solvent. As lipases are the preferred enzymes, such esterification reactions can be conducted under mild conditions.

More specifically, the present invention is a method for the preparation and tailoring of at least one carboxyl acid group of a selected polymer generally comprising the steps of:

(1) selecting a polymer;

(2) selecting an alcohol;

(3) selecting a catalyst, typically an enzyme;

(4) combining the polymer with the alcohol in a reaction vessel to create a reaction mixture;

(5) adding the enzyme to the reaction mixture and allowing an esterification reaction to proceed; and (6) isolation of the product polymer.

The reaction polymer can be selected from the group consisting of those that contain carboxylic acid pendant groups.

The alcohol can be selected from the group of molecules containing one alcohol group (monofunctional) or greater than one alcohol group (polyols). Some suitable illustrative monofunctional alcohols having sensitive groups include but are not limited to 2-azido-3-hydroxy propanal, 2-hydroxyethyl methacrylate (HEMA), propargyl alcohol, hydroxyethoxy silanes (silicone functionality), 3-cyano benzyl alcohol, 1-H-benzotriazole-1-methanol, 3(trimethylsilyl)propargyl alcohol, 2-thiophene methanol, perillyl alcohol, 4-(trimethylsilyl)phenethyl alcohol, 4-(triphenylsilyl)benzyl alcohol, cinamyl alcohol, 4-nitrocinamyl alcohol, allyl alcohol, γ-linolenyl alcohol, arachidonyl alchohol, crotyl alcohol, furfuryl alcohol, retinol, trans-3-(trimethylsilyl)allyl alcohol, and trans,trans-2,4-hexadiene-1-ol. Some suitable illustrative polyols include but are not limited to ethylene glycol, glycerol, erythritol, xylitol, ribitol, sorbitol, 1,2,6 hexane triol, 1,2,4- butanetriol, 4,4'-oxydibenzyl alcohol, 4,4'-sulfonyldibenzyl alcohol, glucose, D-glyceraldehydes, D-erythrose, D-threose, D-ribose, D-arabinose, D-xylose, D-lyxose, D-allose, D-altrose, D-glucose, D-mannose, D-gulose, D-idose, D-galactose, D-talose, D-dihydroxyacetone, D-erythrulose, D-ribulose, D-xylulose, D-psicose, D-fructose, D-sorbose, D-tagatose, D-sorbitol, D-mannitol, D-glycerol, D-myo-inositol, D-gluconic acid, D-glucaric acid, D-δ-gluconolactone, D-δ-glucuronolacone, D-glucuronic acid, L-ascorbic acid, L-dehydroascorbic acid, α-D-α-D-gluco-1-phosphate, α-D-gluco 6-phosphate, 2-deoxy-D-ribose, 2-deoxy galactose, L-fucose, L-rhamnose, D-glucosamine, D-galactosamine, N-acetyl-D-glucosamine, N-acetyl-D-muramic acid, N-acetyl-D-neuraminic acid), 2-methacryloxyethyl glucoside, oligosaccharides (e.g. maltose, lactose, sucrose, raffinose, cyclodextrins) and derivatives of such saccharides, maltose, sucrose, and lactose, and the like.

The enzyme can be selected from the group consisting of hydrolytic enzymes. Some suitable illustrative families of hydrolytic enzymes from which the enzyme can be selected include but are not limited to lipases, proteases, and esterases.

Further, the present invention also comprises the polymers prepared by the method, some of which are novel compositions of matter, and others of which would have been difficult or impossible to prepare by conventional synthetic methods. For example, the present invention can result in the synthesis of a range of both new and known polymers. In some cases, the polymers obtained by the present method would have been very difficult to prepare by conventional chemical synthetic methods. In other cases, the polymers obtained by the present method are a less difficult alternative method for producing known polymers. In one embodiment, the enzyme catalyzes the reaction with regioselectively or enantioselectivity.

The esterification reaction is allowed to proceed for a defined time period, which results in an ester bond at the carboxylic acid. As the reaction proceeds, the reaction mixtures can be subjected to a controlled rate of water removal, which can help drive the reaction towards more rapid and higher substitution at the carboxylic acids. The reaction can be quenched at any time and the ester polymer can be isolated at any time thereafter. Thus, the present invention can be used to prepare novel ester-containing polymer and to impart desired qualities therein.

The present method makes use of hydrolytic enzymes to catalyze the polymerization of the reactant monomers in part because such enzymes can catalyze regioselective esterification under bulk flow conditions. Hydrolytic enzymes suitable with the present method include enzymes selected from the group comprising lipases, proteases, and esterases. Preferably, lipases are used as lipases can optimally catalyze reaction under mild reaction conditions. The enzyme used in the process of the present invention may be bound on an inert carrier, for example, an anion exchange resin.

The present method uses a direct enzymatic esterification to modify polymers with pendant carboxylic acid groups by providing a direct route for tailoring polymers though the use of lipase-catalyzed esterification reactions. For example, alcohols such as glycerol can be esterified to the pendant carboxylic acids groups of polyvinyls such as polyacrylic acid. The enzymes catalyze selective esterifications between polyols and pendant carboxylic acids groups along chains of the polymers.

One advantage of the present invention is that it can be used to tailor prepare polymers without the use of the protection-deprotection steps, without the use of organic solvents, and without the use of other harsh aspects and/or chemical methods that were previously required to prepare similar polymers.

Another advantage of the present method is that it can be used with a myriad of polymers that have at least one carboxylic acid pendant group. Such polymers can be selected from the family having carbon-carbon backbones (e.g. polyvinyls) where some fraction of the chain repeat units have carboxylic acid pendant groups. Further, such polymers can be homo- or copolymers where one or more of the repeat units have carboxylic acid pendant groups. Further, the alcohols that are esterified to the pendant carboxylic acids can be mixtures. Hence, one or more alcohols can be simultaneously incorporated into the reaction mixture so that products having one or more types of pendant ester groups are obtained. This will be important when different pendant groups are needed along the polymer chain to provide different properties to the polymer. For example, one pendant ester group can be used for crosslinking and the other for binding of a metal or chemical.

The products of the present invention can be used for a wide variety of uses. For example, such products may be useful as thermoplastic polymers, as protective coatings, sealants, thermosetting paints, as cosmetics, and in other areas like additives for personal care products and in textile finishes etc. The thermoplastic or water-soluble polymers can be cross-linked through chemical or enzymatic reactions of the R-groups to give hydrogel materials or materials that for practical purposes have the properties of thermoset resins.

These features, and other features and advantages of the present invention, will become more apparent to those of ordinary skill in the relevant art when the following detailed description of the preferred embodiments is read in conjunction with the appended drawings in which like reference numerals represent like components throughout the several views.

DETAILED DESCRIPTION OF THE PREFERRED EMBODIMENTS

Introduction

Figure 1:
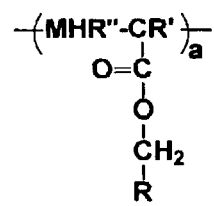
FIG. 1 is a general structure of modified polymers resulting from enzyme-catalyzed esterification of pendant carboxy groups according to the present invention.

The present invention overcomes previous limitations in methods to modify the carboxyl acid side groups of polymers through esterification. Previous methods for the preparation or tailoring of polymers at carboxylic acid pendant groups so that polyols are selectively esterified used protection-deprotection steps to avoid undue damage to the polymer such as the formation of crosslinks between chains. Further, these methods relied on performing the reactions in organic solvents, using carboxylic acids that were activated with electron withdrawing groups, and/or the use of stoichiometric quantities of coupling agents. More importantly, such methods cannot be used to directly modify or tailor polymers at carboxylic acid side chains unless the reactions are performed at high temperatures in the presence of strong acid or a suitable organometallic catalyst. In addition, current methods require protection-deprotection chemistry to avoid crosslinking reactions when the alcohol is a polyol. The current process overcomes these difficulties, which have seriously limited the cost and chemical/physical properties that are attainable for the preparation of polyacids where a fraction of those acids are esterified selectively to a polyol.

The present invention is a new method and resultant compositions that do not require protection-deprotection steps, can be carried out with or without solvent or as bulk reactions, can be carried out with a single hydroxyl component in the reaction or mixed with other alcohols, and results in products that retain general polymer structures with little or no crosslinking that would otherwise render the products as insoluble. Such products can have high molecular weights (e.g. >100 000 weight average). Thus, the catalyzed esterification of the present invention can proceed under bulk flow (solventless) conditions by the direct reaction between selected polymers and alcohols. The method also can be used to tailor the extent of crosslinking between chains.

The present method provides efficient synthetic routes to a wide range of new tailored polymers in a regioselective and/or an enantioselective manner. The regioselectivity of the selected enzymes, such as lipases, allows the direct esterification to polymer carboxylic acids of compounds that have at least one hydroxyl group. The mild reaction conditions used by this new invention allows the hydroxyl containing compounds and/or the polymers to consist of groups that are thermally unstable or are sensitive to acids or organometallic catalysts.

The reaction polymers of the present invention can be polyethers, polyamides, polyesters, polyvinyls, polyurethanes, polycarbonates, polysiloxanes, or any other main chain composition that has one or more carboxyl moieties as pendant groups along the chain. The polymers also can have mixtures of main chain elements such as poly(ester/amides), poly(ether/esters), or any other combination of main chain elements. In addition, chains can be diblock or multiblock where one or more of the blocks have pendant groups that are carboxylic acids. Moreover, the blocks may be so designed so that they have pendant carboxylic groups that differ in reactivity. This can be accomplished by the formation of block copolymers where the blocks differ in stereochemistry, distance of the pendant carboxylic acids from the main chain (e.g. β-aspartate versus γ-glutamate carboxyl groups), or by virtue of some other structural differences between the blocks. By selection of the proper lipase that can differentiate between these blocks that are not alike, carboxylic groups in one of the blocks will react preferentially with the alcohols. The difference in reactivity between the pendant acids in the different blocks may by high or low leading to different extents of reaction at the blocks.

The modified polymers that result from this new invention have application to uses such as tissue engineering (e.g. a component in artificial skin or scaffolds for the growth of cells); membranes (e.g. ultrafiltration and reverse osmosis membranes for dialysis filtration); food and non-food industries (e.g. surfactant and emulsifiers); pharmaceuticals (e.g. delivery of bioactive agents); bioresorbable medical materials; biocompatible implant materials for devices like bone screws and plates; cosmetics (e.g. film-forming agents, shampoos, conditioners); density gradients (e.g. cell separation and diagnostics); plastics (e.g. as polyurethanes after reactions with isocyanate cross-linkers); foams, polyurethane alternative (e.g. rigid foam board stock); hydrogel processed devices (e.g. ophthalmic devices such contact lenses); polyurethane alternatives and compliments (e.g. elastomers, coatings, sealants, or adhesives); polyurethane resins for hot melt adhesives, coatings for vinyl flooring, sealants/adhesives; cast elastomers; and fibers.

Definitions

In this specification, various terms are defined as follows:

"Regioselective reactions" are reactions in which at least two constitutional isomers can be formed from a single reactant but one isomer is observed to be the predominant product of the reaction. Regioselective reactions also can include reactions in which one isomer is formed exclusively. In this invention it refers primarily to the selective condensation of one hydroxyl group contained within a polyol that has 3 or more hydroxyl groups. This also refers to the selective esterification between an alcohol and one of multiple (>2) repeat units that differ in structure but each have pendant carboxylic acid groups.

"Enantioselective reactions" are reactions in which one of the two mirror image molecules (enantiomers) reacts preferentially to form the product. Alternatively, "enantioselective reactions" includes the preferential selection of one of two prochiral sites on an achiral molecule.

"Chemical reactions" can include the formation or dissociation of ionic, covalent, or noncovalent structures through known means. Chemical reactions can include changes in environmental conditions such as pH, ionic strength, and temperature. For example, suitable chemical reactions for the present invention involve the formation of ester bonds between polymer chains that have pendant carboxylic acid groups and alcohols that are present on low molecular weight substrates.

"Bonds," "bonding," and "linkages" are ionic, covalent, or noncovalent attractions of all types.

A "polymer" can be and can include homopolymers, copolymers, and combinations thereof. Polymers normally refer to chains of monomers with at least 10 monomeric repeat units.

An "alcohol" can be any compound with at least one hydroxyl group. An alcohol can include a polyol and can include a compound with only a single hydroxyl group.

A "diol" can be any compound in which there are two hydroxyl groups.

A "polyol" can be any compound in which there are more than two hydroxyl groups. Polyol compounds can include compounds such as carbohydrates.

A "multiol" can be any diol or polyol.

A "polyester" can be any compound in which there are repeat units within a polymer chain that are linked by ester bonds.

Unless otherwise defined, all technical and scientific terms used herein have the same meaning as commonly understood by one of ordinary skill in the art to which this invention pertains. Although methods and materials similar or equivalent to those described herein can be used in the practice and testing of the present invention, suitable methods and materials are described below. In addition, the materials, methods, and examples are illustrative only and not intended to be limiting.

General Methods

1. General Protocol for Enzymatic Condensation Polymerization.

A first embodiment of the present invention is a method for the preparation and tailoring of polymers with pendant carboxylic acid groups that proceeds as catalyzed esterification of a mixture of selected reactants. More particularly, the present method to prepare and tailor polymers with at least one pendant carboxyl acid group uses an enzymatic esterification comprising the steps of:

(1) selecting a first reactant that is a polymer with at least one pendant carboxyl acid group;

(2) selecting a second reactant that is an alcohol;

(3) selecting a catalyst that is a hydrolytic enzyme;

(4) combining the first reactant and the second reactant in a reaction vessel;

(5) adding the enzyme to the reaction mixture and allowing an esterification reaction to proceed; and (6) isolating, such as by precipitation, the product polymer.

The reaction is allowed to proceed for a predetermined period of time sufficient to allow an esterification reaction to occur so that at pendant carboxyl acid group is esterified giving the desired polymer. As the reaction proceeds, a product of the reaction is water, and the reaction mixture can be subjected to a controlled rate of water removal to help drive the reaction towards the product. The reaction can be quenched at any time and the polymer with ester pendant groups can be isolated at any time after the reaction has commenced. The present method can give polymers that are modified or tailored to give products having certain desired physico-chemical properties.

The mixture of the selected reactants with the enzyme can be reacted under bulk flow conditions to regioselectively and/or enantioselectively prepare and tailor polymers with pendant carboxylic acid groups. The reaction proceeds as an esterification and provides a route for direct reactions between selected reactants. The simultaneous modification of pendant carboxylic acids imparts unique characteristics on the resultant polymer, including for illustrative purposes tailoring of the rheological properties, film forming characteristics, interactions with metals, biological compatibility, hydrophilic/hydrophobic balance, and other important changes.

The reactants are selected based their ability to undergo esterification in binary mixtures. Preferably, the selected reactants are chosen because they can partially or completely solubilize with the components of the reaction. In some cases such reactants may otherwise be insoluble but for the reaction conditions.

The present method makes use of hydrolytic enzymes to catalyze the esterification of the selected reactants. Hydrolytic enzymes can be useful to react the mixture because such enzymes can catalyze regioselective esterification reactions under bulk flow conditions. Hydrolytic enzymes suitable with the present method include enzymes selected from the group comprising lipases, proteases, and esterases.

Illustrative preferred enzymes include but are not limited to *Candida antarctica* Lipase B (manufactured by Novozyme), *Mucor meihei* Lipase IM, *Pseudomonas Cepacia* Lipase PS-30, *Pseudomonas aeruginosa* Lipase PA, *Pseudomonas fluoresenses* Lipase PF, *Aspergillus niger* lipase, and *Candida cylinderacea* lipase from porcine pancreatic lipase. Other enzymes that can be used in this invention can be obtained by commonly used recombinant genetic methods such as error-prone PCR and gene shuffling. Furthermore, other suitable enzymes may be obtained by the mining of DNA from various environments such as in soil.

The enzyme can be added to the mixture in a dried state to catalyze the formation of ester bond between the polymers and the alcohols. Alternatively, the enzyme can be added in an aqueous solution and the water subsequently can be removed under vacuum. Some water in the reactions is desirable and every enzyme-catalyzed reaction will have an optimal water content that should be retained in the reaction mixture to achieve optimal reaction kinetics. Such enzymes used in the process of the present invention may be bound on an inert carrier, for instance a polymer such as an anion exchange resin or an acrylic macroporous resin. Other such inert carriers include polypropylene, silica, polyester, or polyurethane resin. When the enzyme is bound on an inert carrier it can easily be removed from the reaction mixture without the need for a purification steps. Enzymes can be bound by physical adsorption or chemical coupling. Further, it is known that lipases, such as Lipase B from *Candida Antarctica*, can be used in either in immobilized or non-immobilized form.

The enzyme may be present in the reaction vessel until the reaction reaches a desired completion. If the enzyme remains in the vessel for an excessive amount of time, the product formed may be further altered by the enzyme resulting in chain degradation, further chain build-up, and/or transesterification. Another possibility is that after excessive reaction times the enzyme can catalyze crosslinking reactions. The enzyme can be removed from the reaction mixture at anytime during the reaction. In some instances, the enzyme recovered from the product had residual activity and can be re-used in subsequent esterifications.

As the present method can include catalyzed esterification by condensations, it can be preferable to adjust the ratio of carboxylic acid to reactive hydroxyl groups 1:1 (equimolar). However, the reaction can proceed with ratios lower and higher than 1:1.

The total reaction time is generally from 30 minutes to 24 hours, preferably from 6 to 20 hours, and more preferably from 12 hours to 18 hours. Preferably, the enzyme is added to the reaction after the reactants have been suitably mixed. The present method can be carried out at from temperatures ranging from 10° C. to 120° C. Preferably, the method is carried out at a temperature between 50° C. and 110° C. Most preferably, the method is carried out at a temperature between 75° C. and 90° C. It should be noted that during reactions in non-aqueous media some enzymes can denature at temperatures significantly higher than 90° C. and that some enzymes may only allow the reactions to proceed relatively slowly at temperatures below 10° C.

The reactants can be heated to predetermined temperatures or to or through a range of temperatures. For example, the reactants can be heated to a temperature in the preferred range and held at that temperature for a predetermined period of time, or for a time sufficient to allow the reaction to proceed to the desired completion. For another example, the reactants can be heated through a range of temperatures within the preferred temperature range, either randomly or in a predetermined pattern. For another example, the reactants can be heated to a first temperature within the temperature range, held at that first temperature for a predetermined period of time, then heated to a second temperature within the temperature range, and held at that second temperature for a predetermined period of time. This procedure can be continued or varied to result in the most effective esterification reaction.

To increase the rate of pendant acid group esterification, or to drive the reaction to completion, it may be necessary to remove water that is evolved during the condensation reaction. The water can be removed from the reaction through numerous techniques well established in the art. For example, the water product of the condensation reaction can be removed by reducing the pressure or applying a vacuum. Alternatively, the water can be removed with a wiped film evaporator under reduced pressure. In another alternative method a desiccant such as a molecular sieve is used, taking precautions to avoid physical damage to supported enzymes due to abrasion between the desiccant and the enzyme support.

The reaction in the present method can be quenched by means understood by person of ordinary skill in the art. For example, the quenching of the reaction can be accomplished by removal of the enzyme from the reaction by a filtration step. To aid in the filtration, minimal amounts of a solvent such as methanol can be added to reduce the viscosity of the product mixture during the filtration process. In some cases the removal of the enzyme can be accomplished by filtration without addition of a solvent. In another alternative, the enzyme can be affixed to the walls of the reactor or a fixed bed column. Thus, removal of the product from the reactor or column results in separation of the enzyme and quenching of the reaction.

After the reaction is quenched, the polymer product can be precipitated by cooling the reaction mixture and/or adding ethylacetate. An alternative method is the use of filtration methods. For example, after separation of the enzyme as above, unreacted low molar mass compounds (e.g. polyols) can be removed by filtration using a low molecular weight cut-off membrane (e.g. <5 000 Kda). Thus, the high molecular weight polymer esterified with a polyol will be retained during the filtration. To reduce the viscosity of the product during the filtration, the addition of a safe solvent such as water may be useful. For some applications, removal of unreacted substances such as glycerol from the product may not be necessary. The product can then be a mixture of the esterified polyacid and a polyol.

The progression of the reaction can be monitored at anytime during the reaction. One method to monitor the progress of the reaction is by withdrawing a portion of the reaction mixture. The portion can be analyzed by techniques such NMR spectroscopy and GPC chromatography. Other methods to test the progression are known to those with ordinary skill in the art.

Figure 10:
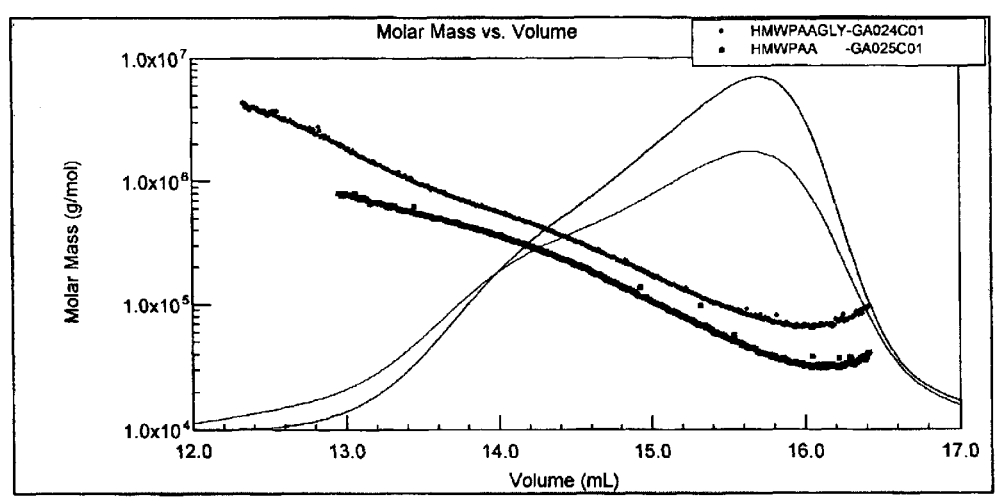
FIG. 10 illustrates the absolute molecular weight of the product as described in FIG. 4 and polyacrylic acid from MALL-LLS-SEC experiment.

The present method generally enables the preparation of both low and high molar mass polyacids that have a desired fraction of their side groups modified with an alcohol. The alcohol can be monofunctional and selected from the family of substances that are chemically sensitive. Alternatively a diol or polyol can be used where the enzyme selectivity links one of the hydroxyl groups to the pendant carboxyl groups. In the case of high molecular weight products, preferably, the resultant polymer is greater than 100 000 ($M_w$) and less than 1 million ($M_w$). More preferably, the resultant polymer is greater than 150 000 ($M_w$) and less than 500 000 ($M_w$). Most preferably, the resultant polymer is greater than 270 000 ($M_w$) and less than 350 000 ($M_w$). In a typical example as shown in FIG. 10, the average molecular weight, determined by a MALLS experiment, is ~358 000. It is understood that one of ordinary skill in the art can tailor the present method to prepare polymers of various molecular weights. Thus, this method is not specific to the formation of products of a certain molecular weight but can be used generally to form products having any desired molecular weight. The product molecular weight will be a function of the starting polyacid chain length, the molecular weight of the alcohol (monofunctional, diol or polyol), the degree of substitution, and the extent (if any) that a diol or polyol reacts in a nonspecific manner to form covalent bonds between chains.

It is understood to one skilled in the art that the present method can be used to form products that are not-crosslinked as well as products with a tailored degree of crosslinking. In some cases a certain extent of crosslinking may be desired. In other applications of this invention, the desired outcome is a higher degree of selectivity where little or no crosslinking occurs during the enzymatic esterification of a polyacid with a polyol. Both little or no crosslinking and the tailoring of certain crosslinking levels can be achieved by this invention. The elimination or introduction of crosslinks will be a function of the enzyme used, the reaction conditions (e.g. reaction time, temperature), and the substrates. The reactions can be tuned to achieve high selectivity or a lower level of selectivity.

The polymers prepared by the present method generally can be modified on pendant groups of the polymers. In many cases, all the pendant carboxylic acid groups on the polymers will not be modified by the alcohols. In other cases, all of the pendant groups will be modified by the alcohols. The degree of modification will depend upon the selected reactants, enzyme, and other reaction conditions (e.g. time, temperature). Also, in some cases where the polymer consists of multiple blocks, the blocks may each contain pendant acid groups that differ in some way. The differences in the blocks may be due to the stereochemistry of the repeat units, the length of the spacer between a pendant acid and the main chain, or the structure of links between repeat units within each block. This difference in the blocks can be used to create differential reactivity of the acid pendant groups in the blocks. Thus, the pendant acid groups in one block may react to a greater extent than the pendant acids within another block within the block copolymer.

One advantage of the present method is that it can allow for the chemical modification of polymers without altering the other side chains or sensitive main chain groups. More specifically, by performing enzyme-catalyzed polymer modification reactions, alcohols are linked to pendant carboxylic acids under relatively mild conditions. As the conditions are relatively mild, the chemically sensitive groups remain relatively unchanged during the esterification. Examples of where this is important include when the polyacid consists of main chains with ester, silicone, phosphate, carbonate, or some other chemically labile groups. Conventional esterification methods will often cleave such bonds where the new enzymatic methods are sufficiently mild to retain the structure of these groups. Alternatively, the sensitive groups can be on the alcohol that is reacted with the polyacid.

Preferred Reactants

As discussed, the present method uses generally at least two types of main reactants. The first reactant is a polymer with at least one pendant carboxylic acid group. The second reactant is an alcohol.

1. Polymers with Pendant Carboxylic Acid Groups

The first reactant is a polymer with at least one pendant carboxylic acid group. While such polymers suitable for the present method are numerous, such polymers include the general formulas (1A and 1B):

General formula 1A is as follows:

$$[R_1-CR_2(COOH)]_n-[R_3]_m \quad (1A)$$

wherein $R_1=CH_2$ or CH(COOH), $R_2$=H, (COOH), or $CH_3$, and $R_3$=Repeat units that can include acrylic acid, methacrylic acid, itaconic anhydride, maleic anhydride, acrylonitrile, ethylene, vinyl acetate, butadiene, ethylene oxide, p-iodostyrene, isobutylene, maleic acid, acrylamide, n-butyl acrylate, methyl methacrylate and the like. The repeat units can be distributed randomly, alternating, in blocks, or in any other pattern along the chain. Instead of two repeat units, the polymer can contain three or more repeat units. The numbers m and n are the number of those repeat units within the polymeric chain.

General formula 1B is as follows:

$$-[(R_4)_a-CR_5(COOH)-(R_6)_b]-(R_7)- \quad (1B)$$

wherein $R_4$ and $R_6$ are generalized groups. For example, these groups can comprise between 1 and 2 carbon atoms. The carbon atoms on these groups can be branched, linear, or cyclic. If these groups are fully unsaturated, then the R-group can be represented as $(CH=CH)_n$, wherein n can range from 1 to 2. Further, these groups can be substituted and may contain a ketone, ester, nitrile, isonitrile, nitrate, sulfate, or phosphate. Alternatively, these groups can contain silicones, heterocylic rings, quaternary ammonium, selenium, phosphate, or sulfate. The subscripts a and b can be 0 to 15.

$R_5$=groups that include but are not limited to H, $CH_3$, COOH.

$R_7$=includes a range of groups that link the repeat units along the chain. The group $R_7$ includes but is not limited to ester, amide, Si—O—Si, ether, amide, phosphate, and the like.

A person of ordinary skill in the art will recognize polymers that can be used with the present method can include one, two or more repeating units that are distributed randomly, alternating, in blocks, or combining different elements of these arrangements. The polymers can all be of the same molecular weight, can have a distribution of molecular weights that may be narrow or broad, and can be combinations of relatively short chains or individual species.

2. Alcohols

The second reactant is an alcohol. Such alcohols can be mono-alcohols and polyols. It is understood that numerous alcohols can be used with the present invention and can be represented generally with the formula (2):

$$HO-R, \quad (2)$$

wherein the R-group represents a generalized group.

The R-group as shown in Formula 2 can comprise between 1 and 30 carbon atoms. The carbon atoms on the R-group can be branched, linear, or cyclic. The R-group can contain various degrees of unsaturation (CH=CH) where alkene groups are isolated or conjugated. Further, the R-group can be substituted and represented generally as $CH_3(CH_2)_{n-1}CH_oR_1(CH_2)_{m-1}$, wherein $R_1$ can be selected from ketones, esters, alkenes, substituted or non-substituted phenyls, alkynes, azides, nitriles, halides, silicones, perfluoro, isonitriles, nitrate, sulfates, and phosphates, n and m can range from 0–20, o can be 0 or 1. Alternatively, the R-group can be substituted and represented generally as $CH_oR_1(CH_2)_{m-1}$ wherein $R_1$ can be selected from ketones, esters, silicones, perfluoro, alkenes, alkynes, azides, nitrites, isonitriles, nitrate, sulfates, substituted or non-substituted phenyls and phosphates, m can range from 0–20, and o can be 0 or 1.

It is understood that the R-group can have one or more unsaturated groups that are isolated or conjugated. The presence of double bonds can result in a cis or trans configuration. Further, the R-group can have at least one triple bond. When the group has more than one double or triple carbon-carbon bond or combination thereof, these bonds can be conjugated or non-conjugated.

Further, numerous polyols also can be used with the present method. Such polyols, as used herein, can be represented generally as Formula 3:

$$R_p(OH)_n, \quad (3)$$

wherein the $R_p$-group is the backbone of the polyols and n is the number of its hydroxyl groups on the polyols. Preferably, the $R_p$-group is selected so that polyols have at least two hydroxyl groups. More preferably, the $R_p$-group is selected so that at least one of the hydroxyl groups on the polyols is a primary hydroxyl group.

$R_p$ in Formula 3 can be selected from an array of structures. In one embodiment, the $R_p$-group can be a carbon-based structure with between 1 to 23 carbons. In others, the $R_p$-group can be selected from the group comprising alkanes, alkenes, and alkynes. In others, the $R_p$-group can also have multiple hydroxyl groups, and be cyclic, branched, and non-branched. It is understood that the $R_p$-group can be substituted, unsubstituted, and/or have degrees of unsaturation.

If the polyol is a carbohydrate, the carbohydrate can be a natural or synthetic sugar. Exemplary sugar-based polyols that are suitable for use with the present method include monosaccharides and oligosaccharides. Illustrative examples of suitable monosaccharides include glucose, D-glyceraldehydes, D-erythrose, D-threose, D-ribose, D-arabinose, D-xylose, D-lyxose, D-allose, D-altrose, D-glucose, D-mannose, D-gulose, D-idose, D-galactose, D-talose, D-dihydroxyacetone, D-erythrulose, D-ribulose, D-xylulose, D-psicose, D-fructose, D-sorbose, D-tagatose, D-sorbitol, D-mannitol, D-glycerol, D-myo-inositol, D-gluconic acid, D-glucaric acid, D-δ-gluconolactone, D-δ-glucuronolacone, D-glucuronic acid, L-ascorbic acid, L-dehydroascorbic acid, α-D-α-D-gluco-1-phosphate, α-D-gluco 6-phosphate, 2-deoxy-D-ribose, L-fucose, L-rhamnose, D-glucosamine, D-galactosamine, N-acetyl-D-glucosamine, N-acetyl-D-muramic acid, N-acetyl-D-neuraminic acid, and derivatives of such saccharides. Illustrative examples of oligosaccharides include maltose, lactose, sucrose, raffinose, cyclodextrins, and derivatives of such saccharides.

Illustrative examples of sugar derivatives that are useful in this invention are alkyl-glucosides. In such a case, a hydroxyl group of the alkyl glucoside reacts to form an ester link with the pendant acid group of the polymer. If alkyl glucosides are used where the alkyl portion is of substantial length (e.g. n-butyl, n-hexyl, n-dodecyl), then hydrophobically modified polymers with pendant acid groups will be formed.

Examples of other alcohols that can be used with the present method include non-carbohydrate polyols. Examples include 1,2,6 hexane triol, 1,2,4-butanetriol, 4,4'-oxydibenzyl alcohol, 4,4'-sulfonyldibenzyl alcohol and oligomers of vinyl alcohol.

The above and other alcohols can be used in any combination that proves beneficial to the properties of the final product or to improve the efficiency of the enzymatic esterification. For example, in the enzymatic modification of polyacrylic acid with mixtures of ethylene glycol and polyols, the ethylene glycol lowers the viscosity of the reaction medium, dissolves all reactants, and is esterified during the process along with the polyol that is added to the mixture. A person of ordinary skill in the art can select alcohols based on their needs and desires. Further, the polymers that can be used with the present method can include copolymers with two or more repeat unit types having any type of arrangement along the chain (e.g. copolymers that are random, block, graft, star). The polymers with pendant acid groups can have a range of molecular weights, and can be combinations of relatively short chains with long chains as well as polymers with discrete molecular weights (e.g. dendrimers, proteins, DNA). As the polymer is modified at the carboxylic acid groups, there can be substantial variation in the remainder of the polymer.

EXAMPLES

An example of useful polymers includes polyacrylic acid and copolymers of acrylic acid with other vinyl monomers. Examples of alcohols that are useful in this invention include polyols, racemic alcohol mixtures, or alcohols that have a chemically sensitive group (e.g. alkynes). Furthermore, the esterification can occur with selectivity (e.g. enantioselectivity and/or regioselectivity). Thus, this invention provides a method by which racemic mixtures of alcohols may be partially or totally resolved by esterification to a polymer chain. Alternatively, prochiral diols can be esterified in such a way that the ester side group is formed with an excess of a single enantiomer. The resulting polymer chain then has pendant groups that are enriched in one stereochemical form. Polymers that can be produced by this invention have the general structure in FIG. 1. In FIG. 1, the polymer chains that contain reactive pendant carboxylic acid groups can be selected from a wide range of different main chain types and the chains can include, but are not limited to, carbon-carbon, amide, ester, ether, and any mixture of these or other types of linkages along the chain.

Figure 2:
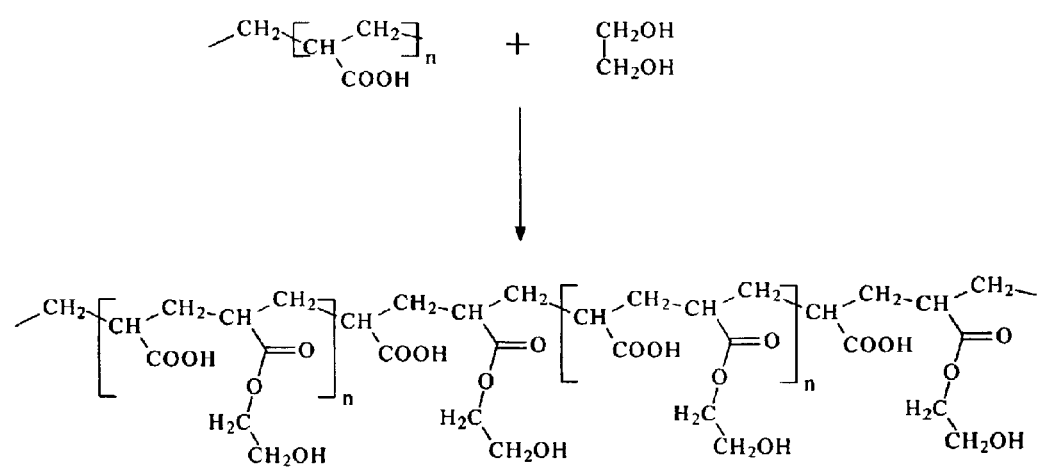
FIG. 2 illustrates the preparation of copolymer of acrylic acid and 2-hydroxyethyl acrylate according to the present invention.
Figure 3:
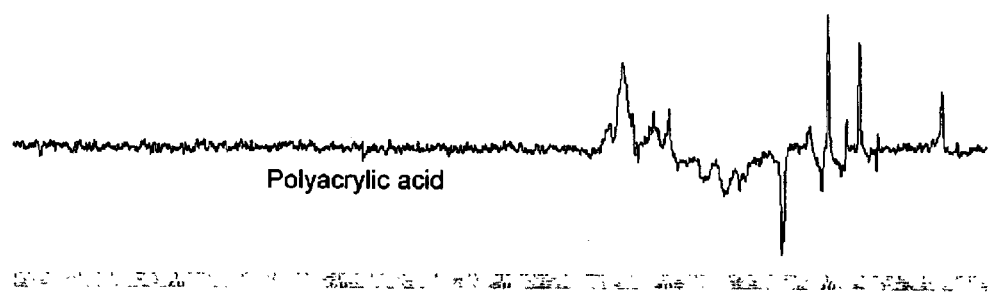
FIG. 3. illustrates the DEPT spectra for the copolymer prepared by the reaction of FIG. 2.
Figure 3:
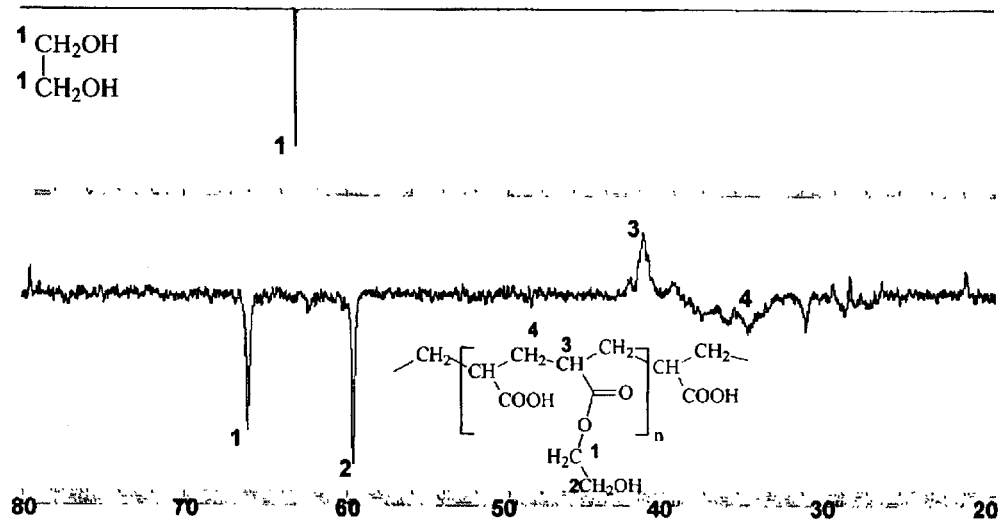

Example 1
Preparation of Copolymer that Contains Acrylic Acid and 2-hydroxyethyl acrylate Repeat Units According to the Reaction Shown in FIG. 2:

To a 100 ml round bottom flask was added 1 part by weight of polyacrylic acid and 3 parts by weight of ethylene glycol. The resulting reactants were stirred at 85° C. for 10 mins. Then, Novozyme-435 (0.1 part) was added and the resulting mixture was stirred for 24 to 36 hrs at 85° C. The vacuum was applied at intervals to remove water liberated from the reaction mixture. After completion of the reaction, the reaction mixture was cooled to room temperature, dissolved in minimum quantity of methanol to filter the enzyme and the product was precipitated by ethylacetate. The resulting product shows that only one of the two hydroxyl groups of ethylene glycol is esterified to the acid pendant group. This high selectivity was determined by different spectroscopic techniques. The splitting of the carbon signal in the DEPT experiment shows in FIG. 3 that, the C-2 carbon in the modified product shifted to 3.1 ppm upfield as compared to the original ethylene glycol signal (FIG. 3), where as the C-1 carbon shifted equally to 3.1 ppm downfield showing that the reaction is highly selective.

Figure 4:
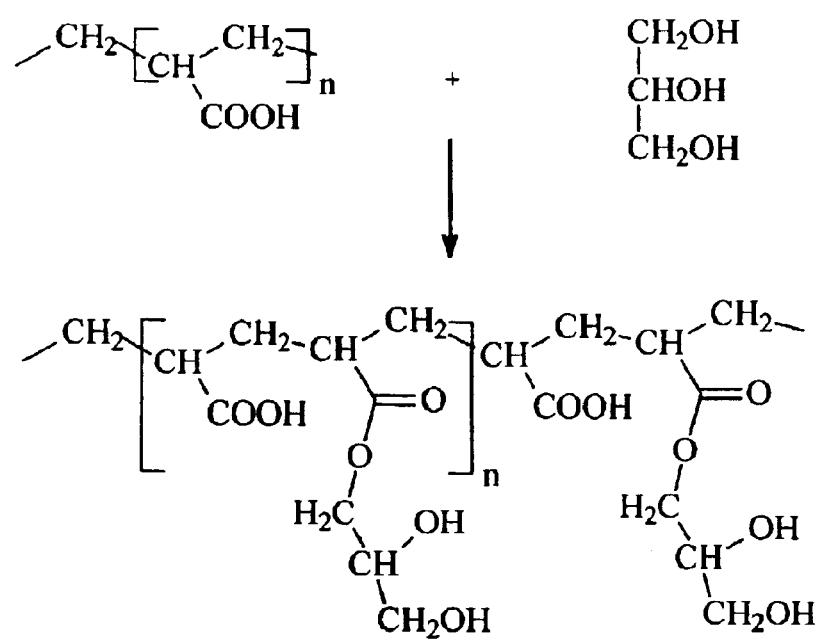
FIG. 4 illustrates the preparation of copolymer of acrylic acid and glyceryl mono-acrylate according to the present invention.
Figure 5:
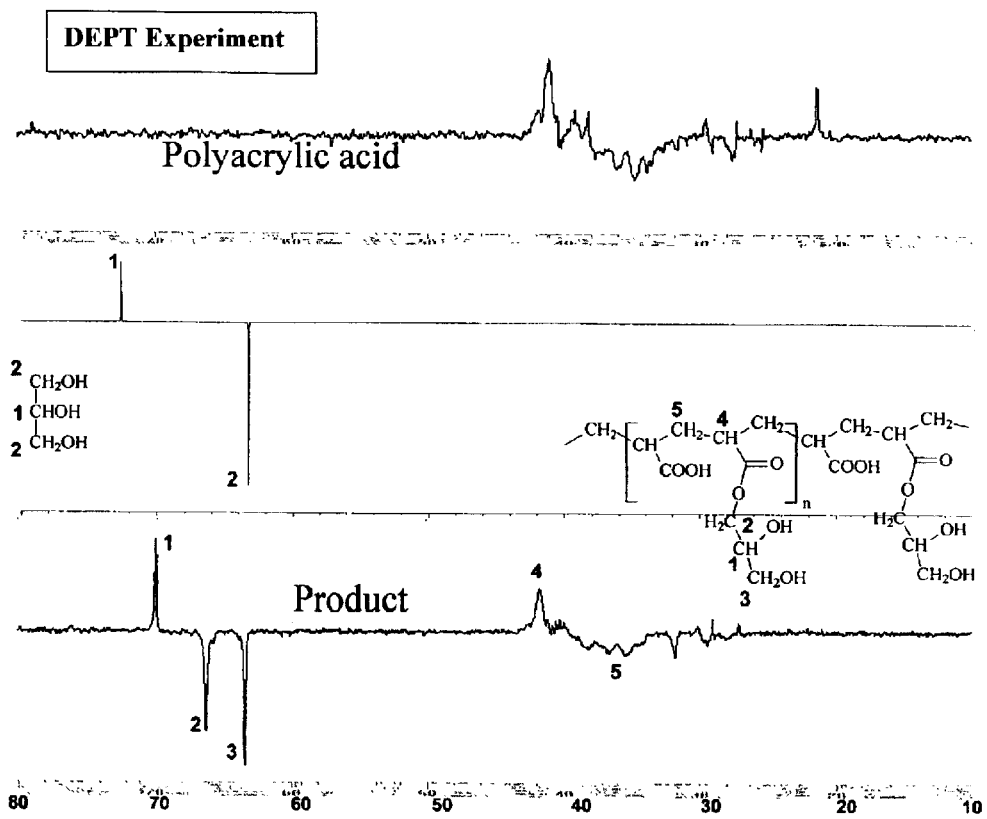
FIG. 5 illustrates the DEPT spectra for the copolymer prepared by the reaction of FIG. 4.

Example 2
Preparation of Copolymer that Contains Acrylic Acid and Glyceryl Acrylate Repeat Units According to the Reaction Shown in FIG. 4:

In a similar way as example 1, to a 100 ml round bottom flask 1 parts by weight of polyacrylic acid and 3 parts by weight of glycerol was added. The resulting mixture was stirred at 85° C. for 10 mins for the proper mixing. The Novozyme-435 (0.1 part) was added to it and the resulting mixture was stirred for 24 to 36 hrs at 85° C. The vacuum was applied sometimes in between (3–4 times) the reaction to remove the water liberated from the reaction mixture to accelerate the reaction. Then the reaction mixture was cooled to room temperature and dissolved in minimum quantity of methanol to filter the enzyme followed by precipitation with ethylacetate. The product was washed with ethylacetate several times to get the pure copolymer. The product shows highly selectivity and characterized by different spectroscopic techniques. The DEPT experiment shows in FIG. 5, that the C-2 signal (reacted one) shifted downfield about 3.0 ppm and simultaneously the adjacent C-1 signal shifted upfield of 2.2 ppm. The unreacted $CH_2$ signal remains at that position, clearly indicating that the reaction is highly selective. The DEPT spectra of the modified product is shown in FIG. 5 with comparison of the glycerol and polyacrylic acid. The average molecular weight was determined by MALL-LLS experiment and also shown in FIG. 10. The MALL-LLS experiment shows the starting material polyacrylic acid having the average molecular weight of $M_w=(1.51\pm0.01)\times10^5$ and the modified product having the average molecular weight of $M_w=(3.58\pm0.04)\times10^5$. From this experiment it can be concluded that the chances of the cross linking is very low or not at all.

Figure 6:
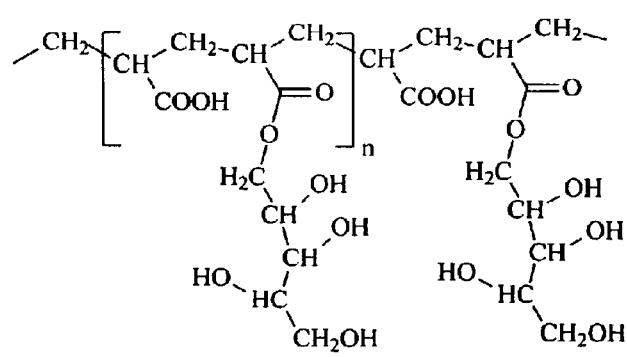
FIG. 6 illustrates the structure of copolymer of acrylic acid and xylityl mono-acrylate prepared according to the present invention.

Example 3
Preparation of Copolymer that Contains Acrylic Acid and Xylityl Acrylate Repeat Units According to the Reaction Shown in FIG. 6:

In a similar way as example 1, to a 100 ml round bottom flask 1 parts by weight of polyacrylic acid and 1 parts by weight of xylitol was added. The resulting mixture was stirred at 96° C. for 10 mins for the proper mixing then cool down the temperature to 90° C. The Novozyme-435 (0.1 part) was added to it and the resulting mixture was stirred for 24 to 36 hrs at 90° C. The vacuum was applied sometimes in between (3–4 times) the reaction to remove the water liberated from the reaction mixture. Then the reaction mixture was cooled to room temperature, dissolved in water. The enzyme was filtered and the crude product was dialyzed to remove the unreacted xylitol. The pure product was dried and analyzed by different spectroscopic techniques. The product shows complete sectivity and characterized by different spectroscopic techniques as described above.

Figure 7:
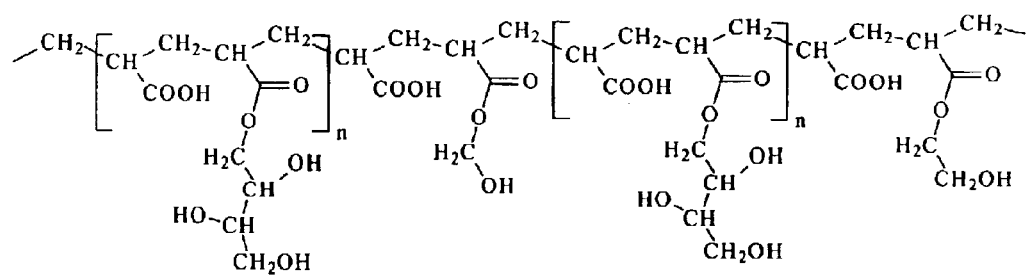
FIG. 7 illustrates the structure of copolymer of acrylic acid, 2-hydroxyethylacrylate and erythrityl mono-acrylate prepared according to the present invention.
Figure 8:
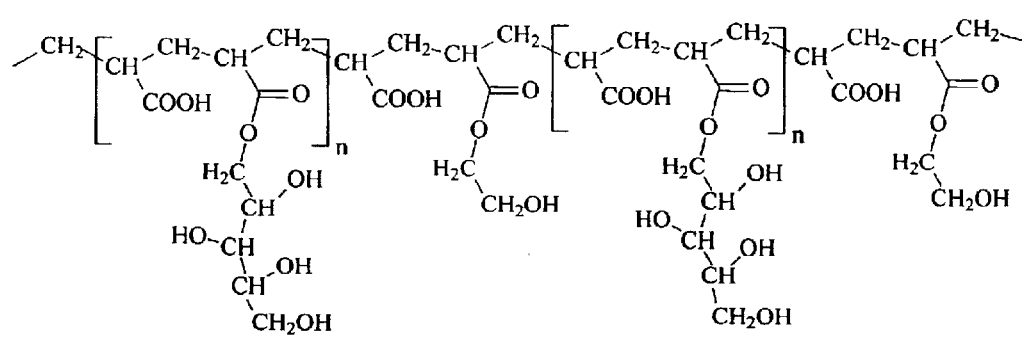
FIG. 8 illustrates the structure of copolymer of acrylic acid, 2-hydroxyethylacrylate and xylityl mono-acrylate prepared according to the present invention.
Figure 9:
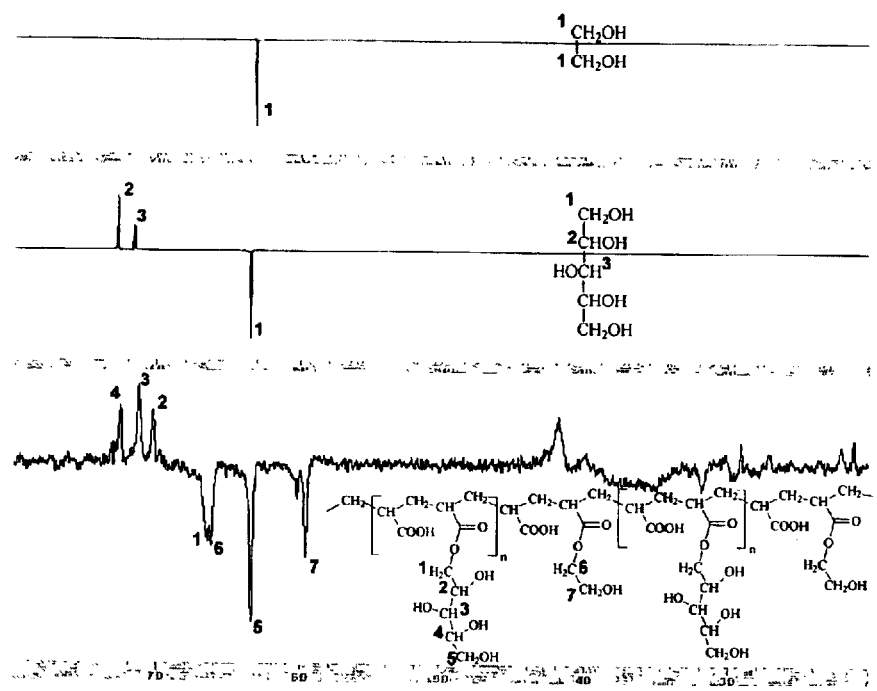
FIG. 9 illustrates the DEPT spectra for the copolymer described in FIG. 8.

Example 4
Preparation of Copolymer that Contains Acrylic Acid, 2-hydroxy ethylacrylate and Erythrityl Or Xylityl Acrylate Repeat Units According to the Reaction Shown in FIG. 7 and FIG. 8:

In a similar way as example 1, to a 100 ml round bottom flask 1 parts by weight of polyacrylic acid and 0.5 parts by weight of ethylene glycol and 0.5 parts of erythritol was added. The resulting mixture was stirred at 90° C. for 10 mins for the proper mixing. The Novozyme-435 (0.1 part) was added to it and the resulting mixture was stirred for 36 hrs at 90° C. The vacuum was applied sometimes in between (3–4 times) the reaction to remove the water liberated from the reaction mixture for the completion of the reaction. Then the reaction mixture was cooled to room temperature and purified as described above in the example 3. The product shows high selectivity and was characterized by different spectroscopic techniques. In a similar way, varying the proportion of ethylene glycol (0.25 parts) and xylitol (0.75 parts) also was taken for the copolymerization as shown in FIG. 8. The product shows high selectivity and characterized by different spectroscopic techniques. As the DEPT experiment shows in FIG. 9, the C-2 signal (reactant one) shifted downfield about 3.0 ppm and simultaneously the adjacent CH-signal (C-2) shifted upfield about 2.4 ppm, clearly indicating that the reaction is highly selective. The effect of ethylene glycol proton is also clearly shown in FIG. 9. The C-6 carbon signal shifted downfield about 3.1 ppm, while the adjacent unreacted carbon C-7 goes upfield about 3.1 ppm, again showing the reaction is highly selective in both the reactant ethylene glycol as well as xylitol. In a similar way, varying proportions of ethylene glycol (0.25 parts) and sorbitol (0.75 parts) were also taken for the co-polymerization.

Example 5

Figure 11:
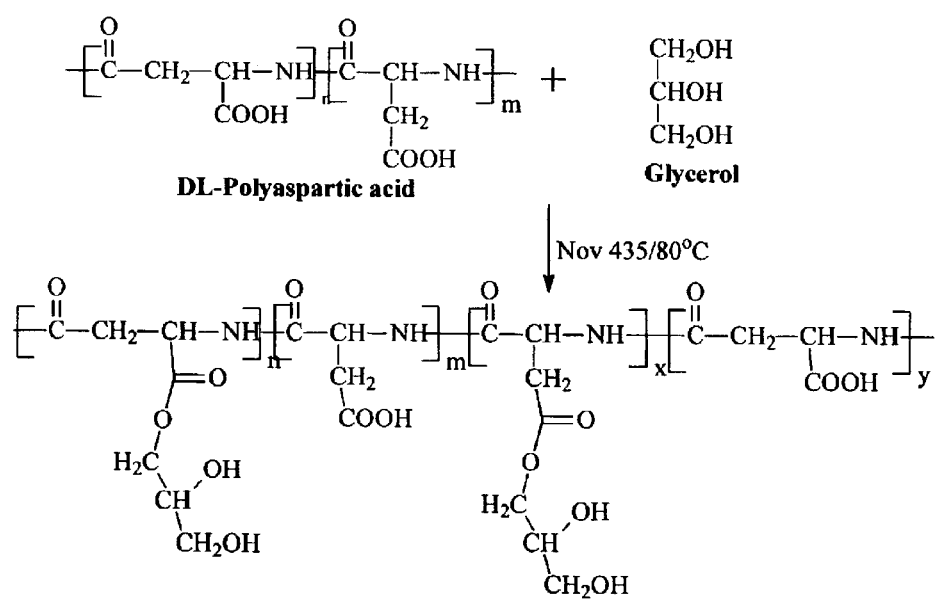
FIG. 11 illustrates the structure of peptide that contains aspartic acid and monoglyceryl aspartate repeat units.
Figure 12:
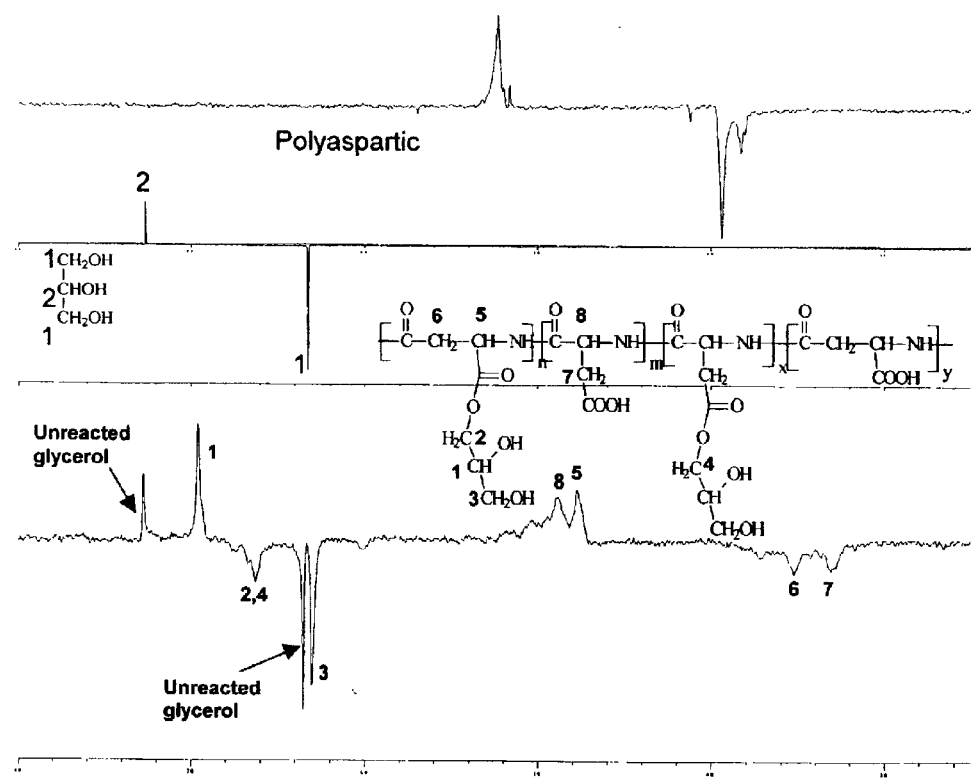
FIG. 12 illustrates the DEPT spectra for the peptide described in FIG. 11.

Preparation of Peptide that Contains Aspartic Acid and Monoglyceryl Aspartate Repeat Units According to the Reaction Shown in FIG. 11:

In a similar way as example 1, to a 100 ml round bottom flask 1 parts by weight of polyaspartic acid and 6 parts by weight of glycerol was added. The resulting mixture was stirred at 80° C. for 1 hrs for the proper mixing. The Novozyme-435 (0.1 part) was added to it and the resulting mixture was stirred for 24 hrs at 80° C. The vacuum was applied sometimes in between (3–4 times) the reaction to remove the water liberated from the reaction mixture for the completion of the reaction. Then the reaction mixture was cooled to room temperature and dissolved in water for the enzyme filtration. The resulting mixture was concentrated and precipitate with cold methanol to get pure product. The product shows high selectivity and was characterized by different spectroscopic techniques. As the DEPT experiment shows in FIG. 12, the C-2 and C-4 signals (reacted one) shifted downfield about 2.75 ppm and simultaneously the adjacent CH-signal (C-1) shifted upfield about 2.15 ppm, whereas the C-3 signal shifting slightly upfield about 0.5 ppm, clearly indicating that the reaction is highly selective.

Example 6

Figure 13:
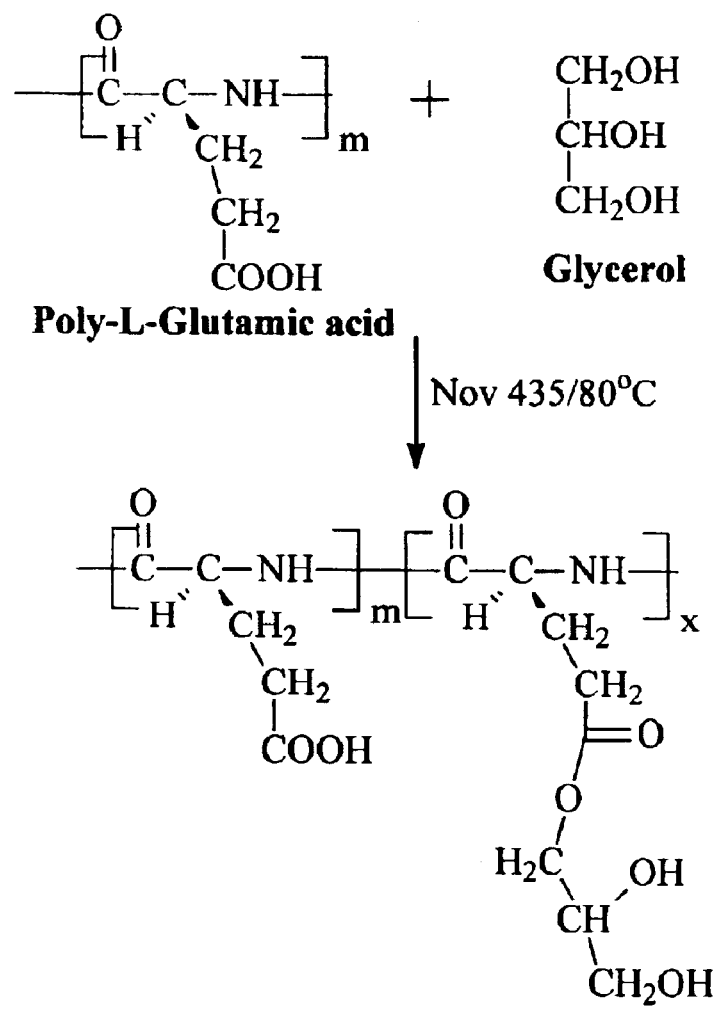
FIG. 13 illustrates the structure of peptide that contains L-Glutamic acid and monoglyceryl glutamate repeat units.

Preparation of Peptide that Contains L-Glutamic Acid and Monoglyceryl Glutamate Repeat Units According to the Reaction Shown in FIG. 13:

In a similar way as example 5, to a 100 ml round bottom flask 1 parts by weight of poly-L-glutamic acid and 6 parts by weight of glycerol was added. The resulting mixture was stirred at 80° C. for 1 hrs for the proper mixing. The Novozyme-435 (0.1 part) was added to it and the resulting mixture was stirred for 18 hrs at 80° C. The vacuum was applied sometimes in between (3–4 times) the reaction to remove the water liberated from the reaction mixture for the completion of the reaction. Then the reaction mixture was cooled to room temperature and dissolved in water for the enzyme filtration. The water was removed by reduced pressure and dissolve in methanol. The methanol soluble portion was taken and precipitated with ethylacetate several time to remove unreacted glycerol. The product characterization was also done with different spectroscopic techniques, showing that the reaction is highly selective, for the methanol soluble portion.

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

What is claimed is:

1. A method for enzymatically synthesizing a modified polymer comprising the steps of:
    a. combining a preselected quantity of an enzyme, a first reactant polyacid selected from the group of polymers having at least one carboxylic acid pendant group, and a second reactant selected from the group of alcohols as a reaction mixture; and
    b. incubating the reaction mixture,
    wherein an esterification reaction occurs between the at least one carboxylic acid pendant group of the polymer and one hydroxyl group of the alcohol to give a modified polymer.

2. The method as claimed in claim 1, wherein the esterification of the polyacid occurs with high regioselectivity to give a product with high molecular weight.

3. The method as claimed in claim 1, further comprising the step of subjecting the reaction mixture to reduced pressure for at least a portion of the time that the reaction mixture is incubated.

4. The method as claimed in claim 1, wherein an enzyme, the polymer, and the alcohol are combined in a reaction vessel.

5. The method as claimed in claim 1, wherein the modified polymer has a regioselectivity of between 85 and 100%.

6. The method as claimed in claim 1, wherein the molar ratio of carboxylic acid pendant groups to the alcohol molecule is approximately 1 to 1.

7. The method as claimed in claim 1, wherein the reaction mixture is heated to a preselected temperature.

8. The method as claimed in claim 7, wherein the preselected temperature is between 50° C. and 120° C.

9. The method as claimed in claim 8, wherein the preselected temperature is between 65° C. and 90° C.

10. The method as claimed in claim 7, wherein the reaction mixture is incubated for a predetermined period of time.

11. The method as claimed in claim 10, wherein the preselected time is between 30 minutes and 24 hours.

12. The method as claimed in claim 10, wherein the preselected time is between 6 hours and 20 hours.

13. The method as claimed in claim 10, wherein the preselected time is between 12 hours and 18 hours.

14. The method as claimed in claim 1, wherein the reaction mixture is heated to between at least two different temperatures in a predetermined pattern.

15. The method as claimed in claim 14, wherein each of the at least two different temperatures is between 10° C. and 120° C.

16. The method as claimed in claim 14, wherein each of the at least two different temperatures is between 50° C. and 110° C.

17. The method as claimed in claim 14, wherein each of the at least two different temperatures is between 75° C. and 90° C.

18. The method as claimed in claim 14, wherein the reaction mixture is maintained at each of the at least two different temperatures for predetermined periods of time.

19. The method as claimed in claim 3, wherein the reaction mixture is subjected to reduced pressure no sooner than 1 hour after the reaction mixture has been heated.

20. The method as claimed in claim 1, wherein the enzyme is a hydrolytic enzyme.

21. The method as claimed in claim 20, wherein the enzyme is lipase.

22. A method for regioselectively tailoring a polymer that has at least one carboxylic acid pendant group by esterification of the carboxylic acid pendant group with an alcohol in the presence of an enzyme, wherein the resulting polymer has at least one unit with the formula —[CH$_2$CH{COOCH$_2$CH(OH)R}]$_n$—.

23. The method as claimed in claim 22, wherein the alcohol is a diol.

24. The method as claimed in claim 22, wherein the alcohol is a polyol.

25. The method as claimed in claim 23, wherein the diol is selected from the group consisting of ethylene glycol, 1,3-propane diol, 4,4'-oxydibenzyl alcohol, and 4,4'-sulfonyldibenzyl alcohol.

26. The method as claimed in claim 24, wherein the polyol is selected from the group consisting of glycol, glycerol, erythritol, pentaerythritol, xylitol, ribitol, sorbitol, 1,2,6 hexane triol, 1,2,4,-butanetriol, glucose, D-glyceraldehydes, D-erythrose, D-threose, D-ribose, D-arabinose, D-xylose, D-lyxose, D-allose, D-altrose, D-glucose, D-mannose, D-gulose, D-idose, D-galactose, D-talose, D-dihydroxyacetone, D-erythrulose, D-ribulose, D-xylulose, D-psicose, D-fructose, D-sorbose, D-tagatose, D-sorbitol, D-mannitol, D-glycerol, D-myo-inositol, D-gluconic acid, D-glucaric acid, D-δ-gluconolactone, D-δ-glucuronolacone, D-glucuronic acid, L-ascorbic acid, L-dehydroascorbic acid, α-D-α-D-gluco-1-phosphate, α-D-gluco 6-phosphate, 2-deoxy-D-ribose, 2-Deoxy galactose, L-fucose, L-rhamnose, D-glucosamine, D-galactosamine, N-acetyl-D-glucosamine, N-acetyl-D-muramic acid, N-acetyl-D-neuraminic acid), 2-methacryloxyethyl glucoside, and oligosaccharides.

27. The method as claimed in claim 22, wherein the alcohol is selected from the group consisting of ethylene glycol and 1,3-propane diol.

28. A method for regioselectively tailoring a polymer that has at least one carboxylic acid pendant group comprising reacting at least one of the at least one pendant carboxylic acids along the polymer chain with a polyol so that at least one hydroxyl group of polyol is esterified to the carboxylic acid in the presence of an enzyme to give the desired modified polymer.

29. The method as claimed in claim 28, wherein the enzyme is a hydrolytic enzyme.

30. The method as claimed in claim 29, wherein the enzyme is lipase.

* * * * *